United States Patent [19]

Li et al.

[11] Patent Number: 5,397,642
[45] Date of Patent: Mar. 14, 1995

[54] ARTICLES INCLUDING THIN FILM MONOLAYERS AND MULTILAYERS

[75] Inventors: DeQuan Li; Basil I. Swanson, both of Los Alamos, N. Mex.

[73] Assignee: The United States of America as represented by the United States Department of Energy, Washington, D.C.

[21] Appl. No.: 874,890

[22] Filed: Apr. 28, 1992

[51] Int. Cl.[6] .............................................. B32B 17/06
[52] U.S. Cl. ................................... 428/403; 210/679; 210/688; 428/405; 428/406; 428/426; 428/429; 428/688; 428/702
[58] Field of Search .............. 428/403, 405, 406, 429, 428/688, 702, 426; 210/679, 688

[56] References Cited

U.S. PATENT DOCUMENTS

| | | | |
|---|---|---|---|
| 4,539,061 | 9/1985 | Sagiv | 156/427 |
| 4,895,705 | 1/1990 | Wrighton et al. | 422/68 |
| 4,935,292 | 6/1990 | Marks et al. | 428/220 |
| 5,078,978 | 1/1992 | Tarbet et al. | 423/22 |
| 5,892,834 | 1/1990 | Rauh | 436/194 |

OTHER PUBLICATIONS

Li et al., J. Am. Chem Soc., vol. 112, pp. 7389–7390 (1990).
Li et al., SPIE Proc., 1337, pp. 1337–1341 (1990).
Rubinstein et al., Nature, vol. 332, pp. 426–429 (31 Mar. 1988).
Wasserman et al. Langmuir, vol. 5, pp. 1074–1087 (1989).
Ulman et al., Langmuir, vol. 5, pp. 1418–1420 (1989).
Putvinski et al., Langmuir vol. 6, pp. 1567–1571 (1990).
Lee et al., J. Am. Chem. Soc., vol. 110, pp. 618–620 (1988).
Allara et al., J. Am Chem. Soc., vol. 113, pp. 1852–1854 (1991).
Tillman et al., J. Am. Chem. Soc., vol. 110, pp. 6136–6144 (1988).
Katz et al., Science, vol. 254, pp. 1485–1487 (6 Dec. 1991).
Dagani, C&E News, pp. 24–30, May 27, 1991.

Primary Examiner—D. S. Nakarani
Attorney, Agent, or Firm—Bruce H. Cottrell; William A. Eklund; William R. Moser

[57] ABSTRACT

Articles of manufacture including: (a) a base substrate having an oxide surface layer, and a multidentate ligand, capable of binding a metal ion, attached to the oxide surface layer of the base substrate, (b) a base substrate having an oxide surface layer, a multidentate ligand, capable of binding a metal ion, attached to the oxide surface layer of the base substrate, and a metal species attached to the multidentate ligand, (c) a base substrate having an oxide surface layer, a multidentate ligand, capable of binding a metal ion, attached to the oxide surface layer of the base substrate, a metal species attached to the multidentate ligand, and a multifunctional organic ligand attached to the metal species, and (d) a base substrate having an oxide surface layer, a multidentate ligand, capable of binding a metal ion, attached to the oxide surface layer of the base substrate, a metal species attached to the multidentate ligand, a multifunctional organic ligand attached to the metal species, and a second metal species attached to the multifunctional organic ligand, are provided, such articles useful in detecting the presence of a selected target species, as nonliear optical materials, or as scavengers for selected target species.

1 Claim, 1 Drawing Sheet

ARTICLES INCLUDING THIN FILM MONOLAYERS AND MULTILAYERS

FIELD OF THE INVENTION

The present invention relates to the field of thin film assemblies or devices and particularly to thin film assemblies or devices useful as, e.g., sensors, nonlinear optical (NLO) materials, and/or trace material scavengers. This invention is the result of a contract with the Department of Energy (Contract No. W-7405-ENG-36).

BACKGROUND OF THE INVENTION

For years, chemists have developed ever more intricate molecules. Recently, chemists have sought to assemble simple molecules into complex, multi-molecule type structures. One developing area is referred to as supramolecular architecture. Typically, supramolecular architecture yields a resultant article having multiple of monolayer films. Within such films, the type of materials may be organic, inorganic or combinations of both and the resultant films offer potential uses in technologies such as, e.g., catalysis, microelectronics, optics and sensors.

For example, Sagiv describes in U.S. Pat. No. 4,539,061 a type of supramolecular architecture wherein built-up films are produced by the stepwise adsorption of individual monolayers. More specifically, Sagiv describes forming on a suitable substrate an ordered monolayer of molecules, such molecules having at least one functional group at one end adapted for attachment to the substrate and at least one non-polar group at another position on the molecule, converting after formation of a first monolayer the non-polar groups to polar functional groups of a reactive nature, and continuing formation of additional monolayers in a like fashion until a desired number of layers is obtained. Since the original work by Sagiv, others have continued to develop such monolayered systems with a variety of different layers.

Another example is shown by Li et al. in J. Am. Chem. Soc., vol. 112, pp. 7389–7390 (1990) which describes multilayered assemblies including silicon dioxide substrates, a silane linking group attached to the substrate, a stilbazole chromophore material attached to the silane linking group, a second silane linking group attached to the chromophore material and a polymeric material attached to the second silane linking group.

Research and study of various monolayered systems has now lead to the development of additional monolayered type assemblies, such assemblies useful in, e.g., binding trace amounts of selected organics and metals.

Accordingly, it is an object of this invention to provide thin film assemblies or devices capable of reacting with and/or detecting trace amounts of selected metals.

It is a further object of this invention to provide thin film assemblies or devices capable of reacting with and/or detecting trace amounts of selected organic materials.

Yet another object of this invention is to provide thin film assemblies or devices capable of use as nonlinear optical materials.

SUMMARY OF THE INVENTION

To achieve the foregoing and other objects, and in accordance with the purposes of the present invention, as embodied and broadly described herein, the present invention provides an article of manufacture including a base substrate having an oxide surface layer, and a multidentate ligand, capable of binding a metal ion, attached to the oxide surface layer of the base substrate.

In another embodiment of the invention, the article of manufacture including a base substrate having an oxide surface layer, and a multidentate ligand, capable of binding a metal ion, attached to the oxide surface layer of the base substrate, further includes a transition metal species attached to the multidentate ligand.

In still another embodiment of the invention, the article of manufacture including a base substrate having an oxide surface layer, a multidentate ligand, capable of binding a metal ion, attached to the oxide surface layer of the base substrate, and a metal species attached to the multidentate ligand, further includes a multifunctional organic ligand attached to the metal species.

In yet another embodiment of the invention, the article of manufacture including a base substrate having an oxide surface layer, a multidentate ligand, capable of binding a metal ion, attached to the oxide surface layer of the base substrate, a metal species attached to the multidentate ligand, and a multifunctional organic ligand attached to the metal species, further includes a second metal species attached to the multifunctional organic ligand.

The multidentate ligand attached to the oxide surface layer can be a multidentate functionalized silane linking group or can be a monolayer of a silane linking group bonded to a multidentate organic moiety such as, e.g., a porphyrin group, such as 5,10,15,20-tetra(4-pyridyl)-21H,23H-porphine.

The present invention also provides a method of detecting the presence of a selected target species including contacting a sensor element including a base substrate having an oxide surface layer, a multidentate ligand, capable of binding a metal ion, attached to said oxide surface layer of the base substrate, and a transition metal species attached to the multidentate ligand with a target sample, measuring the optical absorption of said sensor element exposed to an analyte, and, comparing the optical absorption of said sensor element exposed to the analyte with a standard optical absorption for said sensor element in the absence of the analyte whereby the presence of a selected target species can be determined.

In another embodiment, the method of detecting the presence of a selected target species including contacting the sensor with a target sample, measuring the optical absorption of said sensor, and, comparing the optical absorption of said sensor with a standard optical absorption for said sensor whereby the presence of a selected target species can be determined includes the sensor having a base substrate having an oxide surface layer, a multidentate ligand attached to said oxide surface layer of the base substrate, said ligand capable of binding a metal ion, and a transition metal species attached to the multidentate ligand, and further includes a multifunctional organic ligand attached to the transition metal species.

In still another embodiment, the method of detecting the presence of a selected target species includes contacting a sensor including a base substrate, a multidentate ligand attached to the base substrate, said multidentate ligand including a monolayer of a silane linking group bonded to a monolayer of 5,10,15,20-tetra(4- pyridyl)-21H,23H-porphine with a target sample, measuring the optical absorption of said sensor, and, comparing the optical absorption of said sensor with a standard optical absorption for said sensor whereby the presence of a selected target species can be determined. The target species can generally be either an organic or metal contaminant.

DETAILED DESCRIPTION

Figure 1:
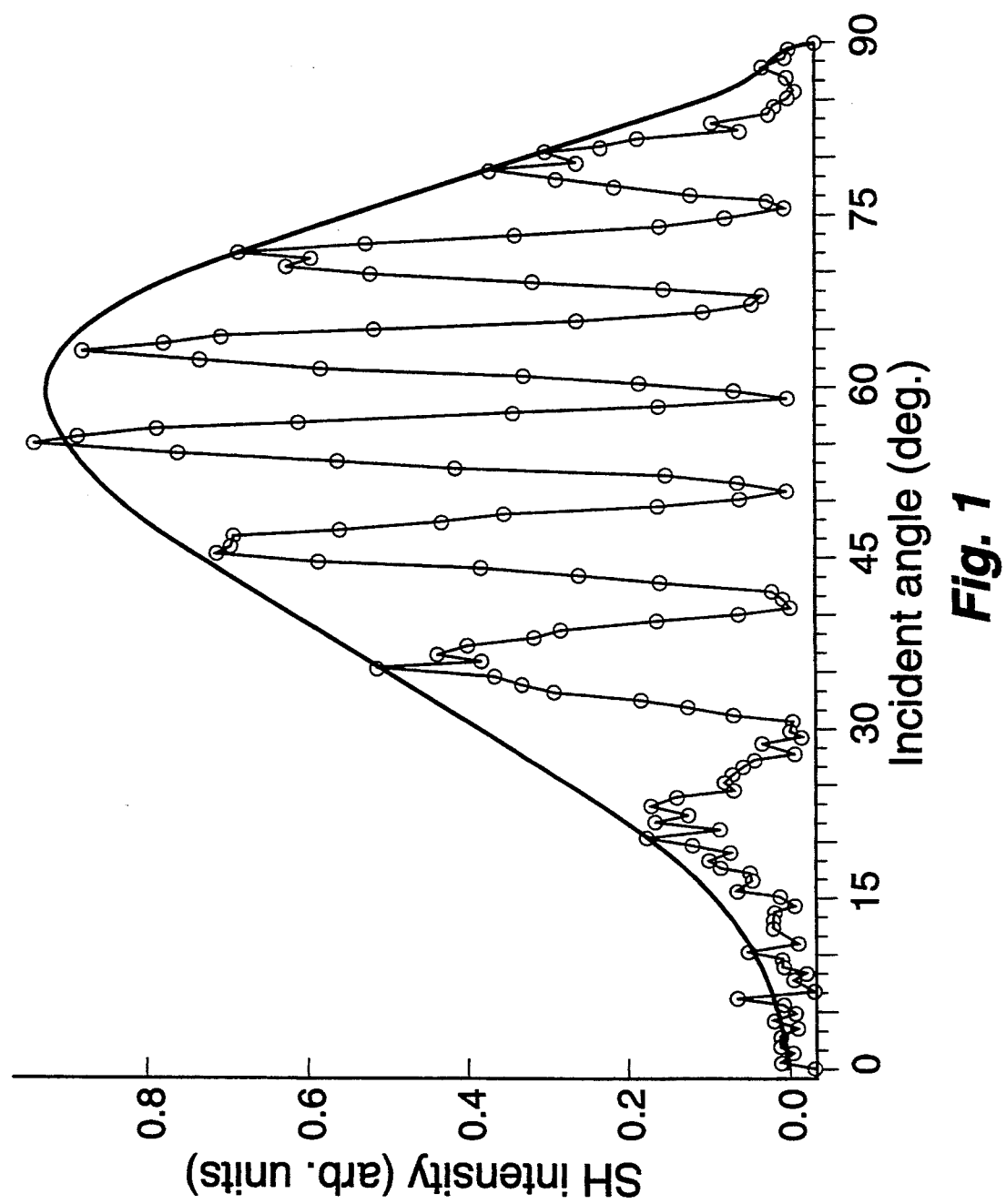
FIG. 1 is a graph illustrating the second harmonic intensity versus the incident angle of the light in an article of the present invention.

The present invention concerns articles including successive build-up of materials, e.g., successive build-up of monolayers of selected materials, to form resultant articles useful, e.g., as trace material sensors or scavengers for organic or metal contaminants, or as nonlinear optical materials for use in, e.g., integrated optics, optical telecommunications or optical computing, and may be useful as, e.g., photovoltaics. The present invention further concerns methods or processes of detecting selected target species using the articles of the present invention.

The base substrate in the present articles should have an oxide surface layer for suitable binding of a subsequent material or layer. Generally, the base substrate can be selected from among quartz, silicon, titanium oxide, zinc oxide, indium-tin oxide (ITO) coated glass, mica, and glass. The preferred base substrate will depend upon the particular application, e.g., for chemical sensors based upon optical transduction, the substrate should preferably be quartz or glass for optical transmission. The base substrate can generally be in any suitable shape or configuration, e.g., in the form of a solid sheet or film, in the form of a powder, e.g., as a silica powder, or in the form of a fiber, e.g., a porous fiber optic.

The initial material attached to the base substrate, i.e., bound to the oxide layer of the base substrate, is generally referred to as a linking group. Such a linking group can generally be a functionalized silane, i.e., a silane including functional groups, such as para-(chloromethyl)phenyltrichlorosilane, para-(iodomethyl)phenyltriiodosilane, 3-aminopropyltrimethoxysilane, 3-cyanopropyltrichlorosilane and the like. The functionalized silane can also include secondary functionality, e.g., a multidentate functionality capable of binding metal ions. Exemplary of such a functionalized silane containing secondary funtionality capable of binding a metal ion is N-[(3-trimethoxysilyl)propyl]ethylenediaminetriacetate (TMPEDTA). The linking group material or monolayer can be joined to the base substrate as a single material as in the case of, e.g., N-[(3-trimethoxysilyl)propyl]ethylenediaminetriacetate and the like wherein a single material contains both desired functionalities, or the material or monolayer can be formed by a combination of materials, e.g., a silane functionality obtained from, e.g., a chloromethylphenyl trichlorosilane joined to, e.g., a material such as a porphyrin ring to achieve the multidentate ligand functionality capable of binding selected metal atoms. In this fashion, the silane functionality serves to anchor the material to the oxide layer and the porphyrin functionality serves as the multidentate ligand capable of binding selected metal atoms. Such resultant materials may be used to scavenge selected metal ions from, e.g., aqueous systems or may be used as a detector for selected metals or organics by observing the electronic perturbation upon, e.g., the porphyrin ring in the presence of certain organics or metal contaminants.

The multidentate ligand can further be a multifunctional ligand. By the term "multifunctional" it is meant that the ligand has at least two separate types of functional groups, while by the term "multidentate" it is generally meant that there are at least two coordinative groups either of the same or differing molecular structure that can serve as binding sites with a subsequent material. Generally, the ligand attached to the base substrate will be multidentate and may further have additional functionality. In some instances where further binding through multiple binding sites is not sought, the ligand can be multifunctional without being multidentate. In those cases, the multifunctional ligand may or may not allow for further chain extension-type growth.

In another embodiment, the resultant article including the base substrate and the multidentate functionality joined through an appropriate linking functionality to the base substrate can have an additional material or monolayer joined to the multidentate ligand. Such a subsequent monolayer or material can be a metal layer generally formed from any metal capable of binding to the multidentate ligand, e.g., from an alkali metal, an alkaline earth metal, a transition metal, a rare earth metal, or an actinide metal. Preferably, the metal is an actinide metal or a transition metal, more preferably a transition metal such as, e.g., ruthenium(II), ruthenium(III), iron(II), iron(III), osmium(II), osmium(III), mercury(I), mercury(II), copper(I), copper(II), zinc(II), cadmium(II), platinum(II) or platinum(IV). Typically, such a metal can be attached to the multidentate ligand of the preceding resultant material by replacing a labile ligand upon the metal. The resultant materials may be used to scavenge selected organic contaminants from, e.g., aqueous systems or may be used as a detector for selected metals or organics by observing the optical transduction, by electrochemistry, e.g., cyclic voltammetry, or by a mass loading determination, e.g., by a frequency shift of a surface acoustic wave (SAW) device or by a lamb wave device (LW), in the presence of certain metal or organic contaminants.

In another embodiment, the resultant article including the base substrate, the multidentate functionality joined through an appropriate linking functionality to the base substrate, and the metal, e.g., the transition metal monolayer or material can have still an additional material or monolayer joined to the metal material or monolayer. Such a subsequent monolayer or material can be an organic moiety layer formed by attachment of a suitable organic moiety to the transition metal, such a suitable organic moiety having at least two reactive sites whereby a first reactive site binds to the transition metal of the preceding resultant article and the second reactive site remains available for subsequent binding reactions. The organic moiety layer can be formed from, e.g., pyrazine, cyanide, dicyanobenzene, or a pyridine-type structure, e.g., two pyridines linked directly together such as a dipyridyl or through an intermediate group. Such resultant materials may be used to scavenge selected metal ions from, e.g., aqueous systems or may be used as a detector for selected metals or organics by observing the the optical transduction, by electrochemistry, e.g., cyclic voltammetry, or by a mass loading determination, e.g., by a surface acoustic wave (SAW) device or a lamb wave device, in the presence of certain organic or metal contaminants.

The resultant article including the base substrate, the multidentate functionality joined through an appropriate linking functionality to the base substrate, the metal, e.g., the transition metal monolayer or material, and the organic moiety may have still an additional material or monolayer joined to the metal material or monolayer. Such a subsequent monolayer or material may be a second metal layer, e.g., a transition metal layer, formed from metal ligands similar to those used in forming the first metal layer. Preferably, the second transition metal layer will include a metal site having a differing oxidative state than the first transition metal layer. Such a system may provide for a sensor for the detection of trace contaminants or a second harmonic generator for nonlinear optical applications.

In some instances, the articles of the present invention can be tailored to have reversible metal or organic binding. Such a reversible binding may be desirable where an article is used to bind a particular metal contaminant, e.g., selected actinide metals, and subsequently separate the metal contaminamt from the article by application of appropriate electrochemical techniques. Similarly, articles including mixed valence metal layers, i.e., metal layers having differing valences, may provide tunability to the article. Such tunability may provide enhanced properties such as reversible binding of target organic or metal species or of nonlinear optical properties.

In another embodiment, multiple layers of a multidentate ligand such as a porphyrin can be attached to an article through suitable linking groups capable of joining together more than one of such multidentate ligands. For example, a multifunctional material such as a dichloromethylbenzene and the like can be reacted with a first layer of a porphyrin such as 5,10,15,20-tetra(4-pyridyl)-21H,23H-porphine whereby one of the chloromethyl functionalities attaches to the porphyrin ring while the other chloromethyl functionality remains accessible for further reaction and a subsequent layer of the porphyrin material can then be reacted with the accessible chloromethyl functionality. This process can be repeated to build up additional thickness of the multidentate ligand, e.g., the porphyrin material. Such a thicker layer or combinations of layers of the chromophore, i.e., the porphyrin, can be advantageous for resultant nonlinear optical properties.

The article including the base substrate and the porphyrin materials such as 5,10,15,20-tetra(4-pyridyl)-21H,23H-porphine can provide second order nonlinear susceptibility valves about ten times those valves obtained by KDP systems.

The present invention also provides a method of detecting the presence of a selected target species including contacting a sensor element including a base substrate having an oxide surface layer, a multidentate ligand, capable of binding a metal ion, attached to said oxide surface layer of the base substrate, and a transition metal species attached to the multidentate ligand with a target sample or analyte, measuring the optical absorption of said sensor element exposed to the target analyte, and, comparing the optical absorption of said sensor element exposed to the analyte with a standard optical absorption for said sensor element in the absence of the analyte whereby the presence of a selected target species can be determined.

Further, the present invention provides a method of detecting the presence of a selected target species including contacting the sensor element with a target sample or analyte, measuring the optical absorption of said sensor, and, comparing the optical absorption of said sensor element exposed to the target analyte with a standard optical absorption for said sensor element in the absence of the analyte whereby the presence of a selected target species can be determined includes the sensor having a base substrate having an oxide surface layer, a multidentate ligand attached to said oxide surface layer of the base substrate, said ligand capable of binding a metal ion, and a transition metal species attached to the multidentate ligand, and further includes a multifunctional organic ligand attached to the transition metal species.

In still another embodiment, the method of detecting the presence of a selected target species includes contacting a sensor element including a base substrate, a multidentate ligand attached to the base substrate, said multidentate ligand including a monolayer of a silane linking group bonded to a monolayer of 5,10,15,20-tetra(4-pyridyl)-21H,23H-porphine with a target sample or analyte, measuring the optical absorption of said sensor element, and, comparing the optical absorption of said sensor element exposed to the target analyte with a standard optical absorption for said sensor element in the absence of the analyte whereby the presence of a selected target species can be determined. The target species can generally be either an organic or metal contaminant.

The sensor elements described above differ in the number of materials joined or layered together and may generally perform as sensor elements in combination with appropriate sensor systems well known to those skilled in the art of analytical chemistry.

The present invention is more particularly described in the following examples which are intended as illustrative only, since numerous modifications and variations will be apparent to those skilled in the art.

EXAMPLE A

A hexaaquaruthenium(II) complex was prepared according to a slightly modified literature procedure. To $RuO_2$ (2.5 grams(g)) in an argon purged system, $NaIO_4$ (12.5 g), and ice cold $H_2SO_4$ (50 milliliters (ml), 50%) were added. The volatile product, $RuO_4$, was then swept into two consecutive 1 Molar (M) $H_2SiF_6$ baths with a total volume of 200 ml, the baths containing activated lead of 17.5 g and 5 g respectively. After two days, the aqueous $H_2SiF_6$ baths turned purple indicating formation of $[Ru^{2+}(H_2O)_6] \cdot [SiF_6]$. The $Pb^{2+}$ was removed by addition of 2M $H_2SO_4$ (50 ml) followed by filtration. The resulting purple solution was diluted and loaded onto a Dowex W50X8 column which was thoroughly washed sequentially with 1M HCL, water, and 0.1 M para-toluenesulfonic acid (Htos). The product eluted with 1.8 M para-toluenesulfonic acid. The red-purple solution was concentrated under vacuum at about 30° C. Upon cooling, the $[Ru^{2+}(H_2O)_6] \cdot 2tos$ was obtained and rinsed with excess ethylacetate to remove the Htos residue.

EXAMPLE 1

A fused quartz substrate was ultrasonically cleaned in a detergent solution for about 10 minutes, held in a refluxing solution of 1 percent by weight $Na_4(EDTA)$ for about 10 minutes, and then subjected to another 10 minutes of ultrasonic cleaning. Finally, the substrate was rinsed with deionized water, acetone and then exposed to an argon plasma for several hours.

The cleaned quartz substrate was heated at 70° C. in a $5.0 \times 10^{-3}$M N-[(3-trimethoxysilyl)propyl]ethylenediaminetriacetate (TMPEDTA) solution adjusted to a pH of from 2 to 3 by addition of concentrated HCl for three days. The solution was cooled to room temperature and after rinsing with deionized water, the substrate was immersed in a 0.1M buffer solution of HAc/KAc (having a pH of about 5.5) for about 2 to 3 hours with 10 minutes of sonication every half hour. The resultant coated substrate was then sonicated three times in water for about 1 minute, rinsed with deionized water and rinsed with acetone.

The resultant substrate was analyzed by IR using a Bio-Rad FTS-40 with a Harrick Seagull variable-angle reflection attachment. The monolayer of the TMPEDTA was studied using the internal total reflection mode in which the resultant article was pressed against a ZnSe hemisphere crystal with sufficient pressure to assure optical contact. As single attentuated total reflection from the interface of ZnSe crystal and the resultant substrate was collected with 64 scans and 2 cm$^{-1}$ resolution yielding a peak at 1730 cm$^{-1}$ (C=O), and bands at 2848 and 2924 cm$^{-1}$ (CH$_2$) indicating the presence of the TMPEDTA layer.

EXAMPLE 2

The quartz substrate coated with the TMPEDTA monolayer was immersed in 10 ml of a degassed solution of Ru$^{II}$(H$_2$O)$_6$.2tos ($3.6 \times 10^{-2}$M). The temperature of the solution was maintained at less than about 30° C. for about 6 hours with periodic sonication. The resulting substrate included a layer of covalently attached [TMPEDTA]Ru$^{II}$(H$_2$O) was rinsed with deionized water.

EXAMPLE 3

The substrate from example 2 was rinsed with deionized water and then placed into an aqueous solution of $3.6 \times 10^{-2}$M pyrazine and held at room temperature for 1 hour with periodic sonication. Ellipsometry of the resultant substrate indicated increased thickness after immersion in the pyrizine solution. That the pyrizine reacted with the resultant substrate from example 2 indicated ruthenium had bound to the multidentate EDTA-type ligand.

EXAMPLE 4

A fused quartz substrate was cleaned and reacted with TMPEDTA as in example 1. The substrate was then immersed in 10 ml of a degassed solution of Ru$^{II}$(H$_2$O)$_6$.2tos ($3.6 \times 10^{-2}$M). The temperature of the solution was slowly increased to from about 35° C. to 40° C. and maintained overnight. The resultant substrate included a shiny, smooth, metallic mirror surface upon the quartz surface. The metallic layer had a conductivity of 57.5 ohms per centimeter. The resultant article was analyzed by Rutherford backscattering, electron microprobe analysis, scanning electron microscopy and scanning tunneling microscopy which indicated the presence of the ruthenium metal layer upon the substrate.

EXAMPLE 5

A quartz substrate cleaned as in example 1 was placed into a dry chloroform solution of 0.13M para-(chloromethyl)phenyltrichlorosilane and held at room temperature for about 24 hours. The presence of a layer of the silane upon the oxide surface was determined by the change in the water contact angle, which was less than about 5° for a freshly cleaned substrate and about 50° following the deposition of the organic silane layer. Analysis by IR and UV-vis also indicated the presence of the silane layer.

EXAMPLE 6

The resultant substrate from example 5 was placed into a $1.5 \times 10^{-3}$M solution of 5,10,15,20-tetra(4-pyridyl)-21H,23H-porphine (TPyP) in a 1:9 ratio of ethanol to chloroform for 2 days at 90° C. to form another resultant substrate. Analysis by UV-vis spectroscopy showed an intense absorption at 447 nanometers (nm) indicating quaternization of the pyridyl group. Additional analysis was conducted by IR, x-ray photoelectron spectroscopy (XPS), and secondary ion mass spectroscopy (SIMS) indicating the presence of the porphine material.

The nonlinear properties of the resultant substrate including the layer of 5,10,15,20-tetra(4-pyridyl)-21H,23H-porphine were investigated using second harmonic generation in a transmission geometry. The measurements were made using the 1064 nanometer light from a 30 Hertz neodynium/YAG regenerative amplifier system that provided pulses with about 100 picoseconds temporal width and energies at the thin film surface of 200 to 400 microjoules. The p-polarized incident laser was mildly focused onto the surface. The transmitted second harmonic generation (SHG) signal at 532 nm was separated from the fundamental beam using a dichroic mirror and color filters, passed through a polarization analyzer to select the p- or s-polarized component, and detected using a cooled photomultiplier tube. A gated boxcar integrator was used to measure the transmitted second harmonic signal as the substrate was rotated from the normal incidence (0°) to grazing incidence (90°).

The transmitted p-polarized second harmonic intensity from the polycrstalline quartz substrate having the monolayer of 5,10,15,20-tetra(4-pyridyl)-21H,23H-porphine film on the surfaces of the substrate is shown in FIG. 1 for p-polarized incident excitation. Each data point represents the average of 100 laser pulses. The two major features observed are the broad envelope of the SHG intensity as a function of incident angle and the pronounced interference pattern within the envelope. It is believed that the interference fringes of the SH intensity arise from the interaction of the second harmonic waves from the films on either side of the silica substrate.

EXAMPLE 7

The resultant substrate from example 6 was heated at about 100° C. in a 0.1M dichloromethylbenzene solution in a 1:9 ratio of ethanol to chloroform for about 2 days. The substrate was then sonicated, four times each time for about 2 minutes in the same solvent. A subsequent porphyrin layer was then added as before by placing the substrate into a $1.5 \times 10^{-3}$M solution of 5,10,15,20-tetra(4-pyridyl)-21H,23H-porphine (TPyP) in a 1:9 ratio of ethanol to chloroform for 2 days at 90° C. Analysis by UV-vis showed increased absorption growth of the porphrin peak indicating additional porphyrin binding.

Although the present invention has been described with reference to specific details, it is not intended that such details should be regarded as limitations upon the scope of the invention, except as and to the extent that they are included in the accompanying claims.

What is claimed is:

1. An article of manufacture comprising a base substrate having an oxide surface layer, a monolayer of a linking group attached to said substrate, and a monolayer of 5,10,15,20-tetra(4-pyridyl)-21H,23H-porphine attached to said monolayer of a linking group.

* * * * *